United States Patent
Hietanen et al.

(10) Patent No.: US 7,605,921 B2
(45) Date of Patent: Oct. 20, 2009

(54) SYNCHRONOUS OPTICAL MEASUREMENT AND INSPECTION METHOD AND MEANS

(75) Inventors: Iiro Hietanen, Helsinki (FI); Heimo Keranen, Oulu (FI); Seppo Pyorret, Kello (FI)

(73) Assignee: SR-Instruments Oy, Haukipudas (FI)

( * ) Notice: Subject to any disclaimer, the term of this patent is extended or adjusted under 35 U.S.C. 154(b) by 228 days.

(21) Appl. No.: 10/533,645

(22) PCT Filed: Nov. 4, 2003

(86) PCT No.: PCT/FI03/00814

§ 371 (c)(1),
(2), (4) Date: Jan. 13, 2006

(87) PCT Pub. No.: WO2004/042321

PCT Pub. Date: May 21, 2004

(65) Prior Publication Data

US 2006/0164645 A1    Jul. 27, 2006

(30) Foreign Application Priority Data

Nov. 5, 2002    (FI)    .................................. 20021973

(51) Int. Cl.
G01N 21/86    (2006.01)
G01J 1/22    (2006.01)
(52) U.S. Cl. .................. 356/430; 356/237.1; 250/559.1
(58) Field of Classification Search .................. 356/430, 356/238.1, 237.2–237.5
See application file for complete search history.

(56) References Cited

U.S. PATENT DOCUMENTS

| | | | |
|---|---|---|---|
| 4,871,251 A * | 10/1989 | Preikschat et al. | .......... 356/336 |
| 4,937,449 A | 6/1990 | Kreuzer et al. | |
| 5,047,640 A * | 9/1991 | Brunnschweiler et al. | .......... 250/341.8 |
| 5,245,671 A * | 9/1993 | Kobayashi et al. | .......... 382/150 |
| 5,444,530 A | 8/1995 | Wang | |
| 5,625,196 A | 4/1997 | Williams | |
| 5,640,244 A | 6/1997 | Hellstrom et al. | |
| 5,991,046 A | 11/1999 | Shakespeare et al. | |
| 6,498,646 B1 | 12/2002 | Typpo et al. | |
| 6,674,969 B1 * | 1/2004 | Ogusu | .......... 398/79 |
| 6,917,039 B2 * | 7/2005 | Nicolaides et al. | .......... 250/341.1 |

(Continued)

FOREIGN PATENT DOCUMENTS

DE    195 24 036    7/1996

(Continued)

*Primary Examiner*—Gregory J Toatley, Jr.
*Assistant Examiner*—Rebecca C Slomski
(74) *Attorney, Agent, or Firm*—Young & Thompson

(57) ABSTRACT

A method for finding holes, and other related defects and measuring characteristics of sheets of industrial material. Optical detections systems are constantly plagued by intense ambient light and challenged in accuracy. The invention exhibits a defect detection method and apparatus that is resistant to intense ambient light and is capable of inspecting sheets of material (410, 510, 610, 710) continuously, without integration of long periods. In the invention, synchronous detection between the optical transmitters and receivers is utilized. The invention is applicable for inspecting and measuring materials like paper, metal, rubber, plastic, aluminum foil, copper foil, film, coated metal sheet or any other sheet-like material that could run on a production line. The invention is also applicable for finding special defects like holes, pinholes, scratches, spots, cracks, edge faults, streaks, surface faults or any other conceivable defects.

20 Claims, 8 Drawing Sheets

U.S. PATENT DOCUMENTS

2002/0020818 A1* 2/2002 Mitchell et al. .......... 250/459.1
2004/0253824 A1* 12/2004 Tegeder ...................... 438/696

FOREIGN PATENT DOCUMENTS

| | | |
|---|---|---|
| DE | 199 13 429 | 9/2000 |
| EP | 0 497 649 | 8/1992 |
| EP | 1 030 173 A1 | 8/2000 |
| EP | 0 745 917 B1 | 9/2000 |
| EP | 1 367 385 | 12/2003 |
| FI | 112281 B | 12/2000 |
| GB | 2 371 111 | 7/2002 |
| SU | 1402869 A1 | 12/1986 |
| WO | WO 00/31521 | 6/2000 |

\* cited by examiner

SYNCHRONOUS OPTICAL MEASUREMENT AND INSPECTION METHOD AND MEANS

TECHNICAL FIELD OF THE INVENTION

The invention relates to a method and means for finding defects in materials. In particular, the invention relates to a method for finding holes, spots, edge defects and other related defects and measuring characteristics of sheets of industrial material.

Even more particularly the invention is related to industrial optical systems used for inspecting and measuring products manufactured in a continuous fashion, such as steel, aluminium, papers, foils and plastics.

BACKGROUND OF THE INVENTION

There are numerous optical methods for finding optically visible defects, such as holes or spots in industrial material sheets. Manufacturers of such strip or web materials use optical inspection and measurement systems e.g. for controlling the manufacturing process of the materials in order to improve yield in terms of improved quality, decreased waste and machine down time on the manufacturing line.

The optical measurement systems referred here typically operate online i.e. simultaneously with the product manufacturing and are non-contacting.

Detection of such quality defects as pinholes, holes, spots, scratches, streaks, cracks, cuts, tears or edge defects are important applications where aforementioned optical inspection and measurement systems may be used. Defects or material properties of other kinds may also be measured with the described systems. Web or strip sheet width, length or edge position measurements, are other examples of the possible uses of these systems.

One of the methods in accordance with prior art utilises CCD (Charge Coupled Device) cameras. The operation of a CCD camera cell can be divided into two distinctive periods: the integration period and the readout period. During the integration period the cell is active in terms of light intensity measurement and during the readout period it is not. In a typical CCD camera system each CCD camera cell records the integrated light intensity falling upon it during a certain integration period. The resulting integrated electrical charge is stored in each CCD cell until the cell is read out. Typically the total electric charge generated by the photons is stored in a capacitor in each pixel. As a photon hits a pixel, a small amount of charge is added to the capacitor. This process is called the integration period of the device.

The integration period continues until a certain time has elapsed, and after the completion of the integration, readout period starts. In the readout phase the charge proportional to the incident photon number is observed and recorded, and thus incident photon number can be deduced with certain accuracy. After the readout is complete, the CCD is flushed from the stored charges and a new integration period starts.

For example the ULMA product range from ABB Corporation has utilised CCD cameras in web inspection, please see "ULMA Nti tuote data" product publications for reference from ABB. Earlier ULMA products have also utilized phototransistors generating photocurrent.

FIG. 1 shows a flow diagram explaining the prior art. In phase 101 a material sheet is stationary or is traversed between and/or in front of one or more optical light sources and light detectors. In phase 111 a light source, or several emit light beams and shine the beams on a material sheet. In phase 121 light beam targeted towards the material interacts with the material sheet to be inspected or measured.

In phase 131 light is detected at a light detector or light detectors. The light detector or light detectors convert incident light into photocurrent signals in phase 141. In phase 151 the photocurrent signal is processed and manipulated to determine characteristics of the material. Prior art solutions of this type are found for example from GB 2181834 and GB 2087544 which are cited as reference.

Photo multiplier tubes (PMTs) are also used for inspection and measurement of defects in materials manufactured in a continuous fashion. PMTs are most typically used for detection of pinholes in materials. Holes or pinholes in a material sheet may be detected by using a UV (Ultraviolet) light source or a scanning, laser light source on one side of a material and one or several PMTs on the other side. In this case the PMT or PMTs are used to detect the UV or laser light transmitted through the hole while the material traverses the measurement system.

There are several inherent disadvantages in the prior art. The prior art method of FIG. 1 is prone to ambient light, both optical and electrical noise and the level on signal strength is typically also a problem.

The CCD devices are integrating and imaging devices; there are strict limits on the speed of detection. If the material is traversed faster, the CCD equipment may be unable to photograph the whole surface area of the sheets, due to the latency in integration and image readout. The integration method CCD cameras are based upon is incremental, not continuous, and therefore undesirably slow and unreliable. The integration periods of CCDs are also typically quite long for the purposes of dynamical defect detection.

CCD systems also typically operate with visible wavelengths, and ambient light is therefore a problem. A significant disadvantage of the prior art is that either the system has to be covered from ambient light, or it must bear the errors caused by ambient light. Optical filtering is typically inefficient, as the measurements are done at the same wavelengths as ambient light.

CCD camera systems are imaging systems that produce photograph like, digital images of the material to be inspected or measured. All the image information produced by the CCD camera must typically first be stored in specialized image processing electronics or in computer memory and then transferred and/or analysed in a computer system to distinguish useful measurement information from all unnecessary information. The CCD camera itself cannot discriminate and select inspection or measurement data useful for the user of the system. Especially in large industrial inspection and measurement systems, extensive data storage, transfer and computing capacity is therefore required. In many factories or industrial facilities computer systems of this scale are very expensive and tedious to arrange.

PMTs are mechanically vulnerable and measurement systems based on PMTs are poor in terms of shock or vibration resistance. UV light based PMT systems are also notoriously unstable, as the UV-source lifetime is typically only 1-2 months. Despite basically different wavelengths of the system light source and ambient light, PMTs are also sensitive to ambient wavelengths and ambient light remains a problem. In the edge area of the material under inspection, separate, mechanical edge following light shields must be used along the sides of the material, to prevent the PMTs located at the edge of the material from becoming saturated and therefore non-operational. The mechanical edge following shields are unreliable since these light shields need to be mechanically moved in demanding industrial environments with possible harmful interference with the material to be inspected or measured.

Any moving parts or parts mechanically interacting with the material to be inspected or measured are undesirable because of reliability reasons. For example, the edge followers are prone to cause measurement errors as they are subject to mechanical shear, strain and stress, and may typically move to destroy the calibrations of the delicate measurement system. Design of PMT based UV inspection systems for wide material sheets is quite unpractical due to the extensive demands set on mechanical engineering and high cost.

For clarification the opportunity is taken to define the following terms:

"Light receiver" and "light detector" are used in this application interchangeably. "Light detector" refers with emphasis to the semiconductor part of the light receiving detector and its associated optical, mechanical and electronic parts. "Light receiver" refers foremost to the entire optical, mechanical and electrical arrangement for receiving the light and comprises at least one light detector.

"Synchronisation signal" is a signal that is used to synchronise an emitter and a receiver with respect to waveform, phase and/or frequency of the signal.

SUMMARY OF THE INVENTION

The object of the invention is to relieve and remove some of the aforementioned disadvantages. The invention exhibits an optical inspection and measurement method and means which is resistant to intense ambient light and noise and is capable of inspecting sheets of material continuously, without incremental integration, and without losing information.

It is a further object of the invention to produce only data required for the inspection or measurement, at data production rates that are relatively low compared to prior art. An even further embodiment of the invention is to measure a wide diversity of different properties from the material sheet with a single optical inspection and measurement method and means.

Various embodiments of the invention may be constructed of solid-state components and are therefore mechanically more reliable and shock and vibration resistant compared to the prior art. One object of the invention is not to require use of mechanically moving system parts and measure the samples in a non-contacting fashion.

Most of the aforementioned advantages of the invention are achieved with an inspection and measurement method where the basic measurement and inspection signal is the photocurrent generated in a light sensitive electrical component (photoelectric device). This photocurrent is used continuously and directly as the basic measurement and inspection signal. The photocurrent signal appears in the vicinity of a carrier frequency generated in the measurement system for the purpose of synchronised light emission and light detection. The photocurrent is modulated by light interactions with the material to be inspected or measured, and further demodulated in the receiver part to remove the effects of ambient interference, noise and the carrier frequency. Several emitters send beams to a single receiver, and the emitters are synchronised with the detector. The different beams typically have different carrier frequencies, and measure different properties from the sheet.

In one particular embodiment of the invented method, the system comprises at least one LED (Light Emitting Diode) based light source, at least one photodiode based light detector, at least one waveform generator device generating an AC sinewave or square wave control signal, the carrier signal for synchronisation of at least one LED based light source and at least one photodiode based light detector. In this embodiment several phases, processes and arrangements take place to accrue inventive advantages:

a sheet of material to be inspected or measured is traversed between and/or in front of at least one light source and at least one light detector, at least one waveform generator generates an electrical signal (carrier) of a repeating AC waveform at a given frequency for synchronised control and operation of the light source and the light detector, at least one light source emits light, intensity of which follows a carrier waveform of a waveform generator, light emitted by at least one light source is targeted on the material sheet or a part of it and/or the edge of the sheet to be inspected or measured, at least one beam of light is stopped by the sheet, reflects from the sheet, passes partly through the sheet, passes through apertures or holes or defects in the sheet, passes partly by the sheet or otherwise interacts with the material sheet to be inspected or measured in a manner which results in amplitude modulation (AM) of the intensity of the light beam by the material, at least one light detector detects and measures an amplitude modulated light beam signal after it has interacted with the material sheet to be inspected or measured, at least one light detector converts an amplitude modulated light signal it has received into continuous electrical photocurrent, at least one light detector or following analog signal processing electronics of the system, utilize at least current-to-voltage conversion and synchronised detection or demodulation in the further signal processing of the photocurrent signal for improving the quality and signal-to-noise ratio of the inspection or measurement signals of the system, analog signal processing part of the system produces one voltage signal (demodulated signal) for each light detector, the momentary absolute value of the demodulated signal of a light detector is proportional to the amplitude of the modulating effect of the interaction between the light signal and the material sheet to be inspected of measured, demodulated signal amplitude and/or a rapid change in the demodulated signal is observed, recorded and analysed by the inspection or measurement system to measure certain properties of the material sheet, such as sheet width, sheet length or edge position of the sheet, or to locate defects or imperfections in the sheet, such as pinholes, holes, spots, scratches, streaks, cracks, cuts, tears or edge defects in the material, more than one beam from more than one emitter are synchronised with one detector, and different beams measure different properties.

The aforementioned is also considered at the moment to present the best mode of the invention. The best mode of the invention is especially applicable for the purpose of detecting the three-dimensional structure of the defects in the material sheet with multiple light beams synchronised to the same detector.

An optical measurement and inspection method in accordance with the invention comprises at least two light emitters, at least one light receiver, at least one signal generator connected to at least one light emitter and at least one light receiver and means for converting the received light to electrical current, and is characterised in that, a sheet of material lies or traverses between and/or in front of at least two light emitters and at least one light receiver, at least one signal generator controls at least one light emitter and at least one light receiver by sending them a synchronisation signal and thereby synchronises the emission and detection of light rays, at least one signal generator drives at least two light emitters with different carrier frequencies, waveforms and/or phases, and at least one light receiver with both of these frequencies waveforms, and/or phases, at least two light emitters emit at least two rays of light, at least two rays are incident on the stationary or traversing sheet, at least two grazing, transparent and/or reflected rays of light from the sheet or directly from the light emitters are detected by the same light receiver, at least two rays of light are converted to photocurrent, the processed photocurrent and/or changes in the processed photocurrent are diagnosed and observed to find defects and/or determine characteristics of the aid sheet of material.

An optical measurement and inspection arrangement in accordance with the invention comprises at least two light emitters, at least one light receiver, at least one signal generator connected to at least one light emitter and at least one light receiver and means for converting the received light to electrical current and is characterised in that, a sheet of material is arranged between and/or in front of at least two light emitters and at least one light receiver, at least two light emitters are arranged to emit at least two rays of light incident on at least one sheet, at least two grazing, transparent and/or reflected rays of light are arranged to be detected by the same light receiver, at least one ray of light is arranged to be converted to photocurrent by at least one photoelectric device, at least one signal generator is arranged to control at least one light emitters and at least one light receiver by sending them a synchronisation signal and thereby synchronises the emission and detection of rays, at least one signal generator is arranged to drive at least two light emitters with different carrier frequencies, waveforms and/or phases, and at least one light receiver with both of these frequencies, waveforms and/or phases, the photocurrent and/or changes in photocurrent are arranged to be diagnosed and observed to find defects and/or determine characteristics of the said sheet of material.

BRIEF DESCRIPTION OF THE DRAWINGS

Next the invention is described in greater detail with reference to exemplary embodiments in accordance with the accompanying figures, in which.

Some embodiments of the invention are described in the dependent claims.

DETAILED DESCRIPTION

Figure 1:
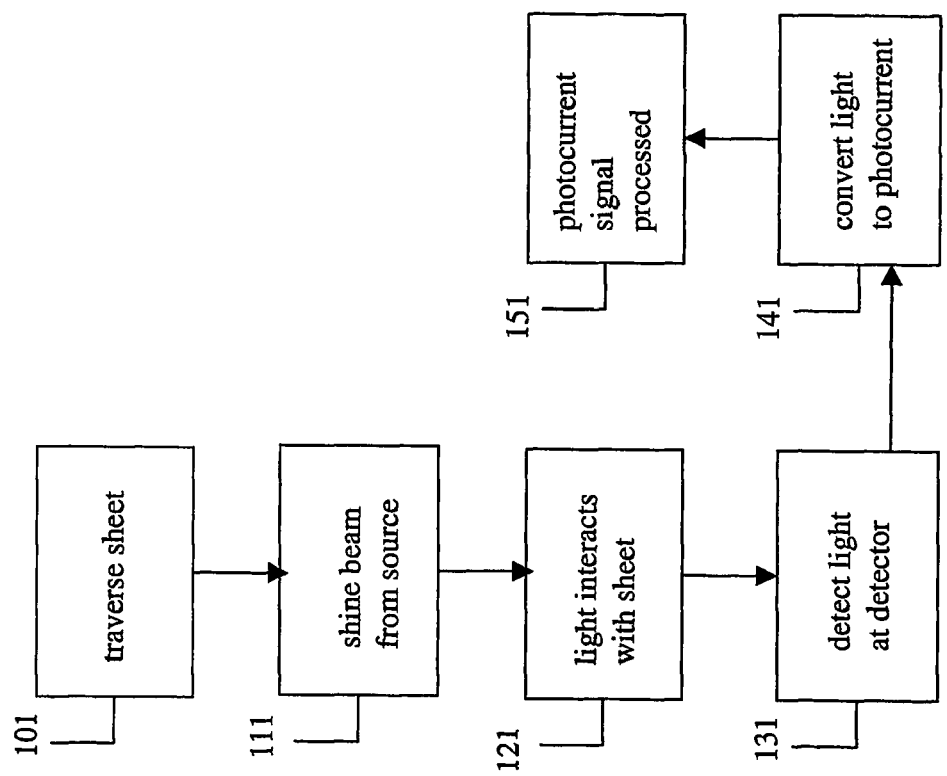
FIG. 1 shows a method 10 in accordance with the prior art as a flow diagram on a general level.
Figure 2:
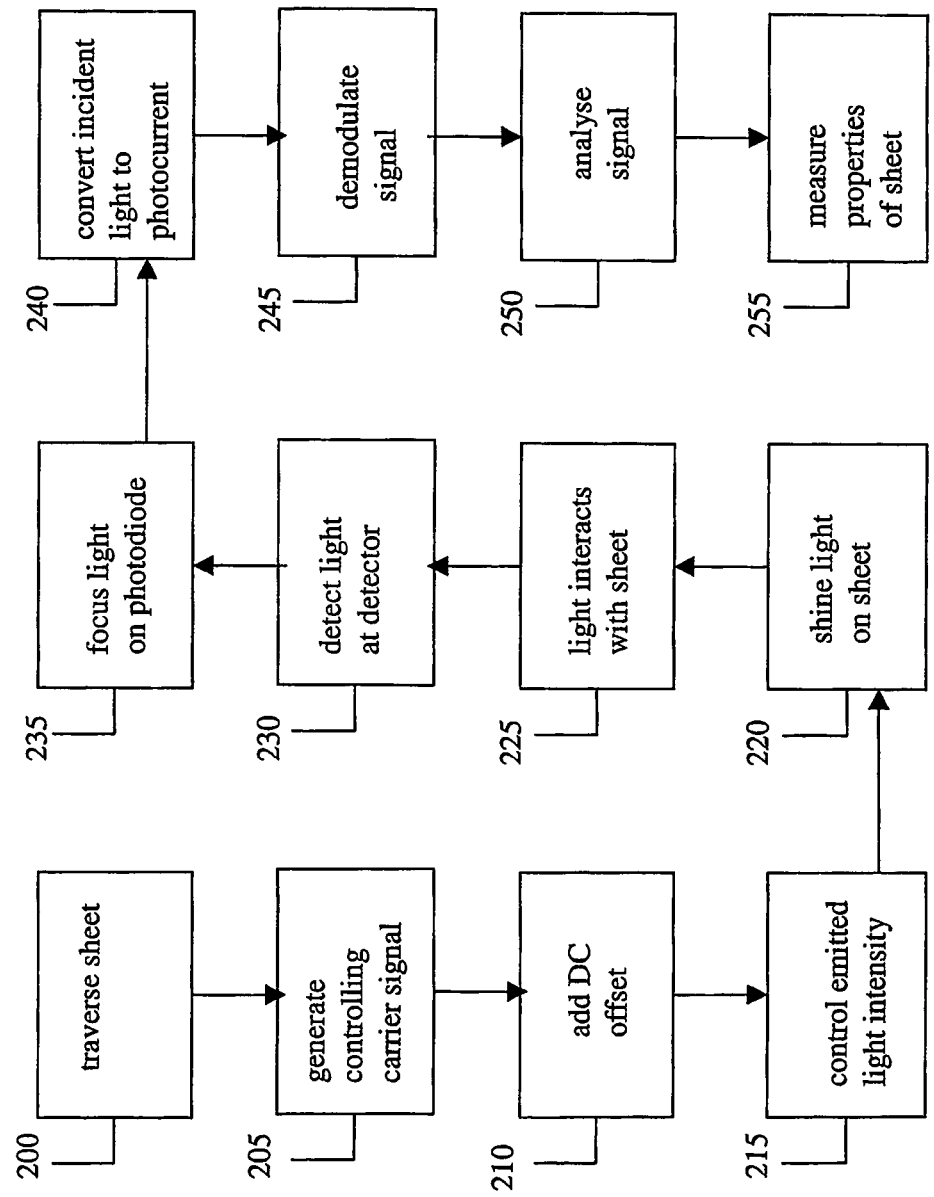
FIG. 2 shows an inspection and measurement method 20 based on synchronised optical detection in accordance with the invention as a flow diagram.

FIG. 2 displays an inspection and measurement method, where synchronous detection in accordance with the invention is used. In phase 200 a material sheet to be inspected or measured lies or traverses between and/or in front of at least one light source and at least one light detector. In phase 205 a controlling, constant frequency carrier signal is generated in a waveform generating device for the purpose of synchronisation of emission and detection of light beams in the measurement system. The carrier may have an AC sine wave, square wave or other waveform. The carrier signal is delivered to at least one light source and at least one light detector for the synchronised control of these system parts. In phase 210 a DC offset may be added to a carrier signal before using it for light source control to guarantee that some light intensity is emitted also at AC control signal values corresponding to lowest emitted light intensity. In some embodiments of the invention DC offset may not be required and phase 210 is therefore optional.

In some embodiments of the invention several waveform generating devices may be used to generate several waveforms and/or several frequencies in order to build measurement or inspection systems where a light detector may simultaneously detect, distinguish and separate light signals originating from different light sources operating at different waveforms and/or waveform frequencies. Several waveform generating devices and waveforms and/or frequencies may also be used for the purpose of isolating two, at least partly independent but closely spaced inspection or measurement systems from each other in terms of light signal disturbance from one system to another. Several emitters and beams may be focused to a particular detector that is synchronised with these emitters. The different beams and emitters may have different carrier frequencies and they may measure different properties from the material sheet. For example, a few beams may depict the three dimensional structure of a defect by measuring its area, height, width, depth, diameter, circumference, reflectivity or the like, properties from which the three dimensional structure may be deduced.

The intensity of a light beam emitted by a light source is controlled in phase 215 by the carrier signal which may have been DC shifted in optional phase 210. The carrier signal is used for controlling at least one light source and/or at least one light detector. In phase 220 the carrier controlled light beam from the light source is shone on the material. The intensity of the light beam follows the waveform of the carrier signal. In phase 225 light beam or beams are incident on the material sheet to be inspected or measured, and light is absorbed and stopped by the sheet, reflects from the sheet, passes partly through the sheet, passes through apertures or defects in the sheet, passes partly by the sheet or otherwise interacts with the sheet. Typically several of the aforementioned or other interactions happen simultaneously or sequentially. Thus the sheet modulates the amplitude of the light signal initially appearing at the carrier frequency and following carrier waveform. In phase 230 interacted and modulated light signal is detected at a light detector. Depending on measurement geometry, inspection or measurement system structure and interactions with the material sheet, a varying amount of light originating from one or more light sources is received by each light receiver in phase 230. In phase 235, a light receiver collimates or focuses the light on a photodiode, APD (Avalanche Photodiode), any other semiconductor based photoelectric, light sensitive component or any other photoelectric device designed for the purpose of detecting light signals. The collimation and/or focusing may be implemented by using light pipes and/or lenses or other optical components. In phase 240 the photoelectric device converts the incident light into photocurrent. The photocurrent is then manipulated and demodulated or in other terms, synchronously detected in phase 245 in order to remove carrier frequency from the signal and to recover the lower frequency, modulated signal of interest. The resulting demodulated signal is proportional to the amplitude of the modulating effect of one or several interactions between the initial, carrier frequency light signal and the material sheet. In phase 250 the demodulated signal is fed into analysis electronics and software for the purpose identifying signals and signal events of interest and the signal is analysed. In phase 255 the absolute value and/or rapid changes in the demodulated signal are observed, recorded and analysed. Analysis results are exploited to measure selected properties of the material sheet, and/or to detect defects or imperfections in the material sheet.

It is clear that within the scope of the invention one or several light sources and one or several light detectors and receivers may be in any line of sight positions with respect to the inspected sheet. Transparent and reflected beams of light as well as light beams interacting by other means may be used in said measurement or inspection systems. In some embodiments phases 200, 205, 210, 215, 220, 225, 230, 235, 240, 245, 250, 255 and 260 may take different permutations in accordance with the invention.

It is also clear that several light beams may have different carrier waveform frequencies in different methods. The different frequencies are useful in distinguishing signals from various emitters at the receiver end. It is therefore possible to route several beams to a particular receiver and use the same receiver in analysing measurements from different optical paths. This allows complex designs of three dimensional detection systems, applicable for detecting defect structures in three dimensions.

Figure 3:
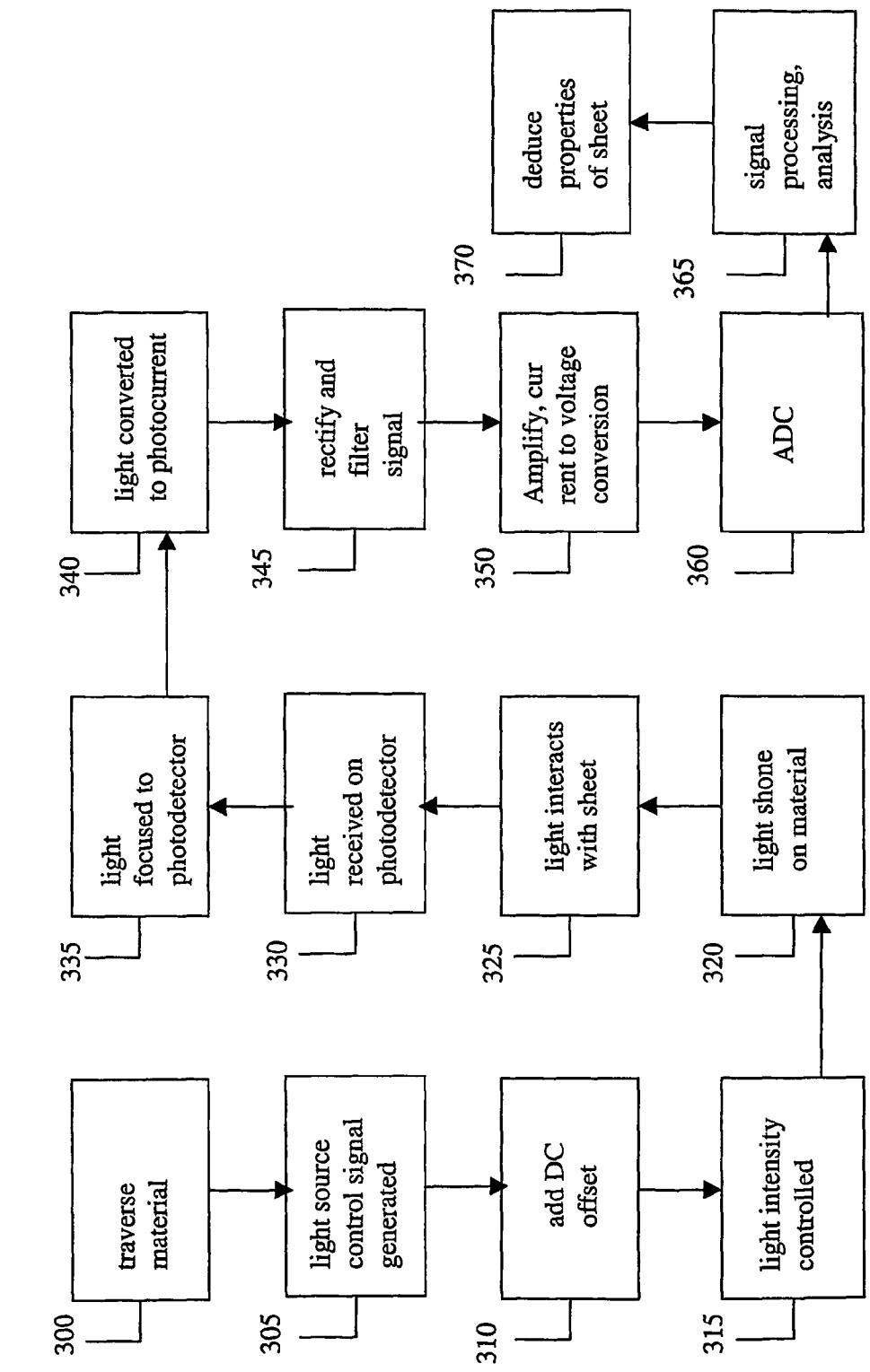
FIG. 3 shows a detailed exemplary embodiment 30 of the invented inspection and measurement method 30 based on synchronised optical detection in accordance with the invention.

FIG. 3 displays one particular and typical embodiment of the invention at a more detailed level. In phase 300 a material sheet to be inspected or measured traverses between and/or in front of one or more light sources and light receivers. In phase 305 a controlling, constant frequency carrier signal of AC sine wave waveform is generated in an electronic signal generator for the purpose of synchronisation of one or several light sources and one or several light receivers in the measurement system. The AC sine wave carrier signal is delivered to at least one light source and at least one light receiver for synchronised operation of the measurement system. In phase 310 a DC offset is added to the AC sine wave carrier signal to guarantee the linearity of at least one emitter.

The intensity of a light beam emitted by a light source is controlled in phase 315 by the DC shifted, sine wave carrier signal. The DC shifted carrier signal is used for controlling one or several light sources. Light sources are LED based, solid state light sources. The DC shifted AC sine wave carrier is directly converted into forward currents signals of individual LEDs in order to implement emitted light intensity signal following the sine wave waveform of the carrier. The light signal intensity therefore consists of a DC component and an AC sine wave component. A square wave signal derived from the AC sine wave carrier signal is used for controlling one or several light detectors. In phase 320 an AC sine wave carrier controlled light beam from a light source is shone on the material. In phase 325 light beam or beams are incident on the material sheet to be inspected measured, and light is absorbed and stopped by the sheet, reflects from the sheet, passes partly through the sheet, passes through apertures or defects in the sheet, passes partly by the sheet or otherwise interacts with the sheet. Thus the material sheet modulates the DC shifted, AC sine wave amplitude of the light signal initially appearing at the sine wave carrier frequency. In phase 330 interacted and modulated light signal is detected at a photodiode based light detector. Light pipes and lenses are used for collimating and focusing light to the active area of a silicon photodiode in phase 335.

In phase 340 the silicon photodiode absorbs the incident light photons and light is converted into photocurrent. A transimpedance amplifier may be used in phase 340 to convert the signal current produced by the photodiode into signal voltage and amplify it.

In phase 345 the control signal (carrier) received by the signal processing electronics from the waveform generator is utilized to perform first step of synchronized detection, rectification of the signal. In this typical embodiment the rectified signal is further low-pass filtered in phase 345 to finalize synchronized detection. The filter circuit used in this embodiment is typically a Bessel filter but may also be a Gaussian-, Chebyshev-, Butterworth- or an RC-filter. Phases 340 and 345 together perform the function of demodulation or synchronised detection in some embodiments.

Manipulation and synchronised detection of the photocurrent signal, which may also be called demodulation of the photocurrent signal, results in that low frequency signal components carried by the carrier frequency are therefore present in the photocurrent signal in the vicinity of the fixed frequency of the waveform generator (the carrier frequency) are effectively amplified and detected whereas signals, noise and disturbance at other frequencies, especially at low frequencies are effectively attenuated. In a typical embodiment of the invention, a fixed frequency AC sine wave voltage is generated by the waveform generator to act as the carrier and a symmetrical, 50% duty cycle, square wave signal, processed from the sine wave signal and carrying equal frequency and phase in term of zero-crossings, is used for rectifying the manipulated photocurrent signal in phases 340, 345 after first removing any DC components of the signal. In this typical embodiment rectified signal is low-pass filtered to finalize synchronised detection, and demodulated voltage signal is produced in phase 350.

In a typical embodiment the absolute value of the demodulated signal is measured and recorded in phase 360 by using an ADC electronics component.

In phase 365 the AC voltage produced is further fed into the signal processing electronics, which performs processing on the basic AC voltage signal. The signal processing electronics may be part of the light detector itself or a part of system level electronics of the inspection or measurement system. The purpose of signal processing is to remove and reduce noise and interference still present in the signal due to e.g. ambient light, other light sources and/or noise present in the signal electronics of the system in general. Synchronised detection heavily depresses the effect of ambient light.

The purpose of the signal processing is also to remove carrier frequency from the signal and to recover the lower frequency, modulating signal of interest phases (345, 350). This step exhibits the key benefits of synchronous detection by removing and reducing noise and interference still present in the signal due to e.g. ambient light, other light sources or system electronics. The resulting signal, demodulated signal is proportional to the amplitude of the modulating effect of one or several interactions between the initial carrier frequency light signal and the material sheet.

It is clear that other waveforms than the aforementioned AC sine wave voltage may be generated by the waveform generator within the range of the invention and other means, including linear demodulation by using a linear signal multiplication instead of square-wave signal rectifying may be used for demodulation or synchronized detection of the photocurrent signal. Quite clearly, the signal that drives the emitter may have a different waveform to the one that synchronises the emitter and a receiver. In one preferable embodiment, sine wave signal is used to drive the emitters, and a square wave signal derived thereof is used to synchronise at least one emitter and receiver.

In some embodiments in phases 350, 360 and 365 the signal output of the signal processing (demodulated signal) is further fed into and processed by system level electronics which may include dedicated electronics to track changes in the demodulated signal which are not normal for the material to be inspected or measured. In a typical embodiment demodulated signal may be further filtered by a low pass filter in one signal path and a comparator circuit may be used to track faster changes of the demodulated signal by subtracting low-pass filtered demodulated signal and the original demodulated signal from each other. In this exemplary embodiment a certain signal difference threshold may be used in the comparator to produce a digital defect pulse when e.g. a hole or a spot is measured by the system.

In some embodiments the absolute value of the demodulated signal may also be observed, recorded and analysed in phases 360, 365 to deduce data intended for locating defects or imperfections in the material to be inspected or measured or especially if certain properties of the material, such as sheet width, sheet length or edge position of the sheet are to be measured.

The digitised signal values produced by the ADC are analysed in phase 365, in the system level digital signal processing electronics and software. The analysis typically produces data depicting the properties of the sheet in phase 370. This data can be made visible to the user of the inspection or the measurement system through a computer monitor but the invented optical detection system may also be integrated with any other production systems or factory automation systems to trigger automatic actions in the production of a materials manufactured in a continuous fashion, such as steel, aluminium, papers, foils and plastics. Likewise the data produced may be accessible to production management software, enterprise resource (ERP) management software or the like in some embodiments.

Quite clearly any electrical or system delays are taken into account when designing the synchronisation of at least one emitter and at least one receiver in accordance with the invention. In some embodiments phases 300, 305, 310, 315, 320, 325, 330, 335, 340, 345, 350, 360 and 370 may take different permutations in accordance with the invention.

Figure 4:
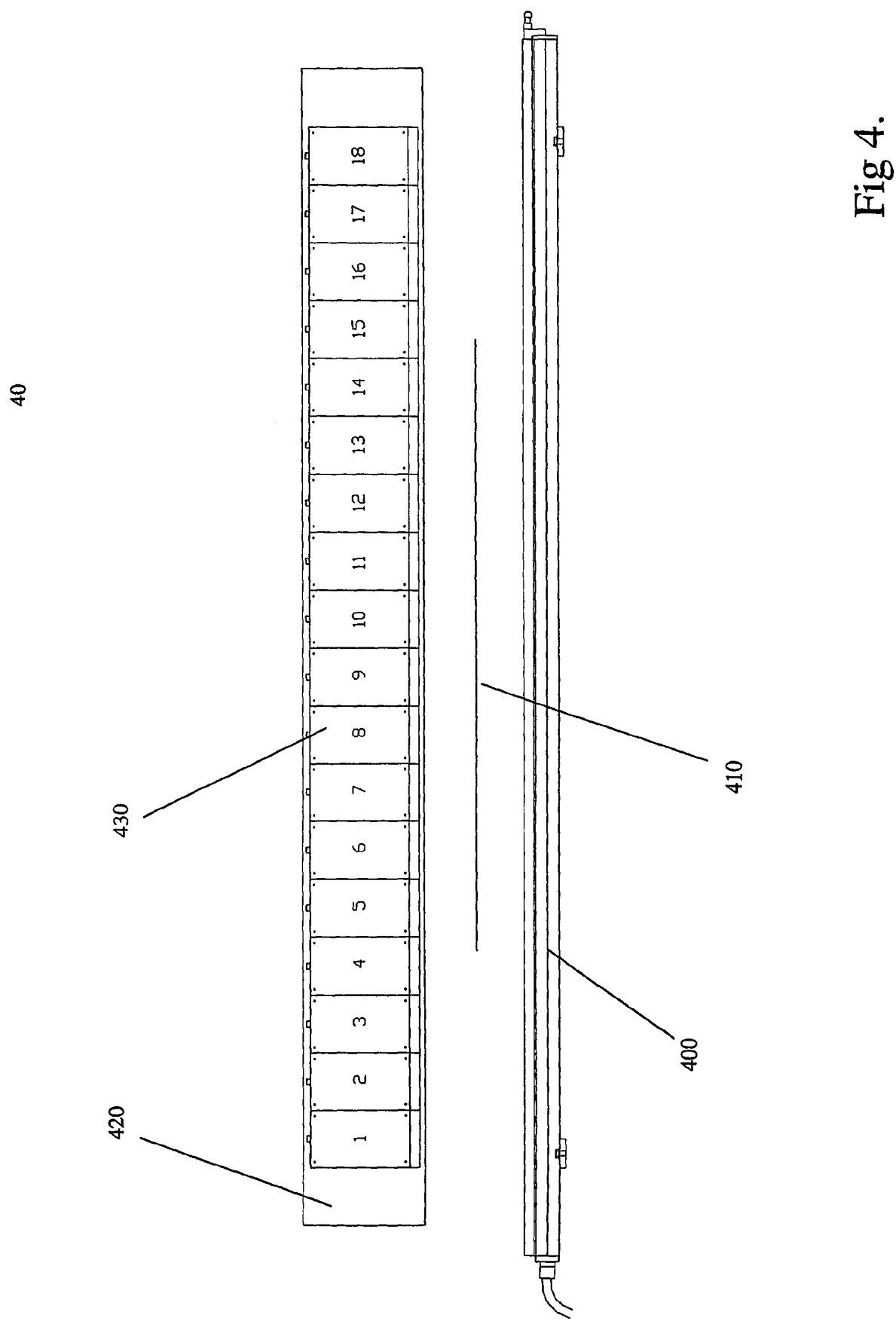
FIG. 4 shows a front view of an arrangement 40 for measurement and/or defect inspection of a material sheet in accordance with the invention.

FIG. 4 shows an exemplary embodiment 40 of the invention where the sheet to be inspected or measured is traversed between a light source 400 and several light detector modules 430. In FIG. 4 the sheet traverses in the direction perpendicular to the projection plane of the figure. In this embodiment the light source is composed of several solid-state, light emitting components such as LEDs (Light Emitting Diodes) and optical components such as light apertures, reflective surfaces, diffusing materials and other components to target the light towards the material sheet and to guarantee uniform light transmission from the light source. The LEDs typically emit light at red wavelengths but blue, white and IR (infrared) LEDs may also be used in some embodiments of the invention. The LEDs may be arranged in one or several rows and a required number of columns to cover the necessary measurement width in the inspection or measurement system. The light source 400 also comprises electronics to receive a controlling, synchronisation signal (carrier) from the waveform generator, and to control the intensity of the light emission from the LEDs or other light emitting components in such manner that the intensity follows the waveform of the waveform generator. In the exemplary embodiment 40 the waveform generated by the waveform generator is an AC sine wave voltage and a DC offset may be added to the synchronisation signal (carrier) before using it for light source control. This is sometimes required to guarantee that sufficient intensity of light is emitted also at the AC sine wave signal values corresponding to lowest emitted light intensity. Adding a DC offset is preferable in embodiments where the LEDs need to be stabilised, but the DC offset is by no means an imperative requirement of the inventive method.

The light detector array 420 consists of several detector modules 430, each consisting of one or more individual light detectors. In this embodiment 40 the light detection of the inspection or measurement system is based on using a total of 18 detector modules. In this exemplary case each detector module 430 comprises 4 light detectors, and therefore a total of 18×4=64 light detectors are used in the system.

The material sheet to be inspected or measured 410 is traversed between the light source 400 and the light detector array 420. In some embodiments the sheet may also be stationary during the measurement. In this embodiment light interactions of interest are those where light passes the sheet, is absorbed in the sheet, transmits through the sheet, passes through apertures or defects in the sheet or otherwise interacts with the sheet in such manner that at least some light detectors receive some intensity of light after those interactions. The material is typically paper, metal, metal foil, coated metal sheet, plastic, rubber, film, or any other sheet like material that could run on a continuous production line. In these materials the defects or imperfections to be detected are typically pinholes, holes, spots, scratches, streaks, cracks, cuts, tears or edge defects. The exemplary embodiment 40 may also be used for the measurement of running sheet width and/or location and/or orientation in an on-line fashion. If the material is produced in sheets of certain discrete length, the length of those sheets may also be measured with the inspection and/or measurement system of this embodiment. Placing the measurement system in a vertical direction would allow measurement of the height of the material with similar arrangement.

Figure 5:
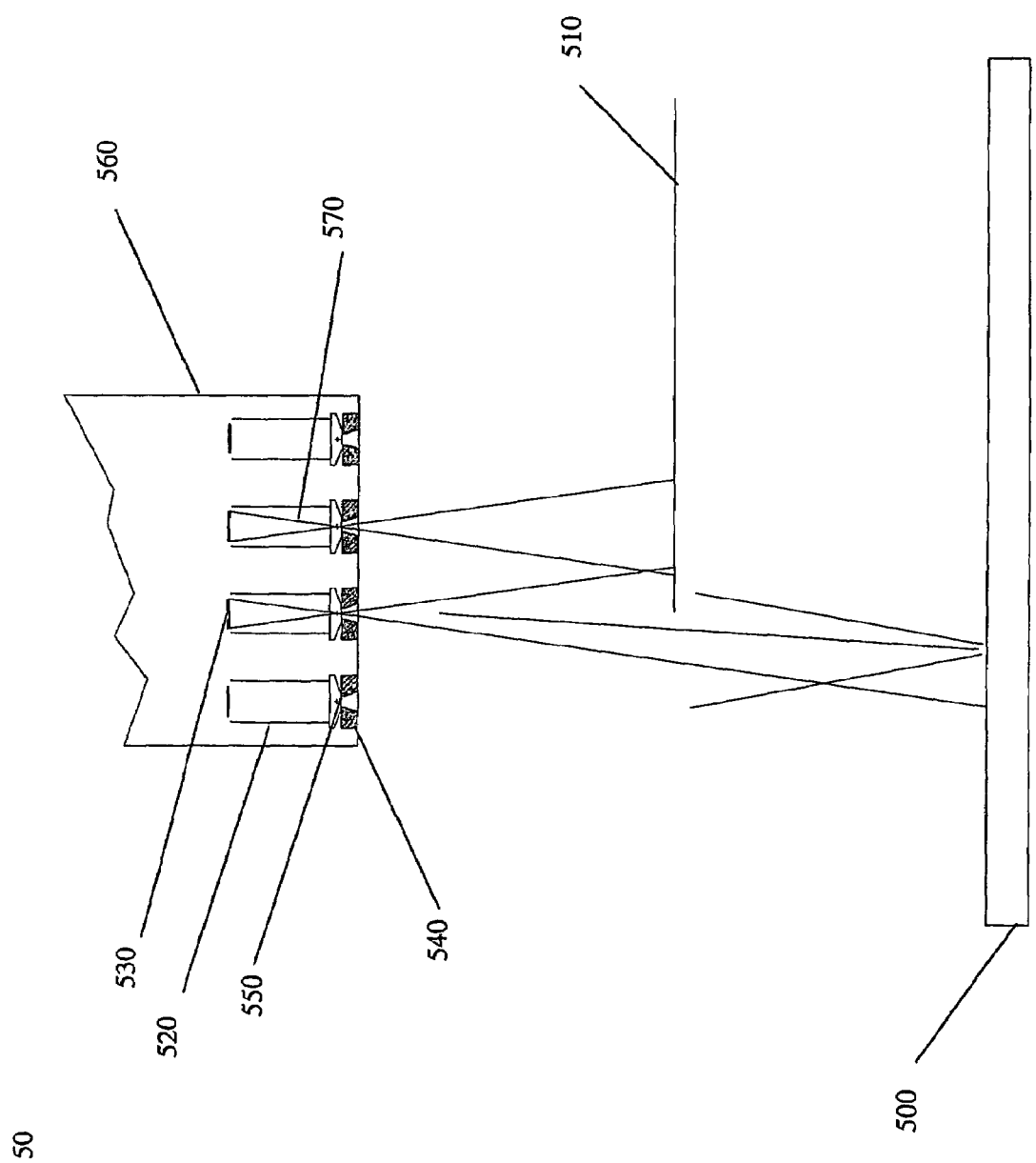
FIG. 5 shows a more detailed front view of an arrangement 50 and an optical ray diagram of an arrangement for measurement and/or defect inspection in accordance with the invention.

FIG. 5 displays a more detailed diagram of four closely spaced light detectors 520 in the exemplary embodiment 50 of the invention. The viewing angle in FIG. 5 is similar to FIG. 4. In this embodiment the light detectors are arranged in detector modules 560, each comprising four light detectors. FIG. 5 shows an exemplary measurement situation in which each light detector is optically arranged to have a certain, limited field-of-view (FOV). In this embodiment the light sensitive optical component is a silicon photodiode 530.

By using other optical components such as a light pipe 540 and a lens 550 the photodiode is arranged to have a limited FOV and therefore only a certain, limited area of the material sheet or surface area of the light source, located behind the material, is viewed by the photodiode. The shape of the viewing area when projected on the surface of the material sheet may be circular, elliptical, rectangular or it may have any other shape as defined by the geometrical and dimensional characteristics of the photodiode and the other optical components. When projected on the surface of the material sheet, the viewing areas of neighbouring light detectors typically overlap. The other optical components 540, 550 define the focusing properties of the optical path from the surface of the sheet to the active surface of the photodiode component. In some embodiments the optics of the light detector may include other optical components and any number of lenses. Optical filters may be used to limit the system operation to a distinct range of wavelengths. Several light detecting photodiodes may use one or more common lenses to comprise several light detectors.

In the exemplary application of detecting and measuring holes in the material sheet, a light detector 570 with FOV covered by the material sheet normally views a certain limited surface area of the material sheet. If the material is non-transparent to the wavelength of light used in the system, the photodiode typically does not receive any significant light intensity originating from the light source. If the material is somewhat transparent to the light used, a certain, but rather uniform amount of light, originating from the light source is transmitted through the material to the light detector. The uniformity of this light signal depends on the uniformity of light transmission through a normal, defect-free sheet of this material. A hole present in the material will inevitably pass through the FOV of one of the light detectors in the inspection or measurement system. This is guaranteed by the fact that the optical measurement system is wider than the material sheet and the FOVs of neighbouring light detectors somewhat overlap. When a hole is in the FOV of a light detector, some light originating from the light source will pass through the hole and will be focused on the photodiode. Depending on hole dimensions, FOV dimensions, material sheet traversing speed, measurement geometry, optics of the light detector and several other factors, this will result in a rapid, momentary change of varying amplitude and length in the total light intensity received by the photodiode. This result is a pulse type, rapid change in the photocurrent output of the photodiode. If this pulse is sufficiently large when compared to any pulse originating from normal variations in the light transmission properties of the material, a reliable hole detection signal may be deduced from the photocurrent output of the photodiode.

Any other defects or imperfections that have the property of transmitting light through the material in a manner clearly deviating from a normal material sheet, may be detected in a similar manner. Defects or imperfections which transmit less light than the normal material, like dark spots may be detected in a partly transparent material in similar manner as the holes except that the polarity of the signal is different. That is, the spot location would be seen as a fast, pulse type decrease in the total light intensity received by the photodiode.

In another exemplary application of measuring the width of a running material sheet, a light detector 520 with FOV located in edge area of the material sheet is viewing partly certain limited surface area of the material sheet and partly the light source 500 located behind the material sheet. If the material is non-transparent to the wavelength of light used in the system, the photodiode 530 typically receives only the light originating from the light source 500 and passing the material. If the material is somewhat transparent to the light used, the photodiode 530 typically receives a certain amount of light originating from the light source 500 and transmitting through the material and a certain amount of light originating from the light source and passing the material sheet. The uniformity of the transmitting light component depends on the uniformity of light transmission through a normal, defect-free sheet of this material. The dynamic range of the inspection or measurement system is arranged in such manner that the photodiode 530 and following electronics do not saturate when no material is present. Therefore the absolute value of the demodulated signal for this light detector may always be measured. The absolute value of the demodulated signal will be inversely proportional to the percentage of this light detector's FOV covered by the material sheet. Larger FOV coverage by the material sheet will result in smaller absolute value of the demodulated signal and vice versa. Less FOV coverage by the material sheet results in larger FOV coverage by the light source 500, which results in higher light intensity in the photodiode and larger demodulated signal. By measuring, normalizing, and calibrating the response of the light detector in terms of demodulated signal values vs. location of the material sheet in the FOV of the light detector, the width of the material sheet may be deduced in the actual industrial measurement situation.

Any other material sheet dimension or location of material sheet edge position may be measured in a similar manner.

It is clear that the light detector 520 presented in this exemplary embodiment of the invention and located at the edge of the material sheet may be used for simultaneous measurement of material sheet dimensions and/or edge location and detection of defects or imperfections in the edge area of the sheet. The optical inspection or measurement system may be arranged to simultaneously record absolute values of the demodulated signal and to track rapid momentary changes in the demodulated signal. Detection and measurement of rapid momentary changes of demodulated signal in light detector 520 is performed in a manner similar to that of light detector 570 operating with a FOV fully covered by the material sheet.

It is also clear that several light beams may have different carrier waveform frequencies in different arrangements. The different frequencies are useful in distinguishing signals from various emitters at the receiver end. It is therefore possible to route several beams to a particular receiver and use the same receiver in analysing measurements from different optical paths. This allows complex designs of three dimensional detection systems.

Figure 6:
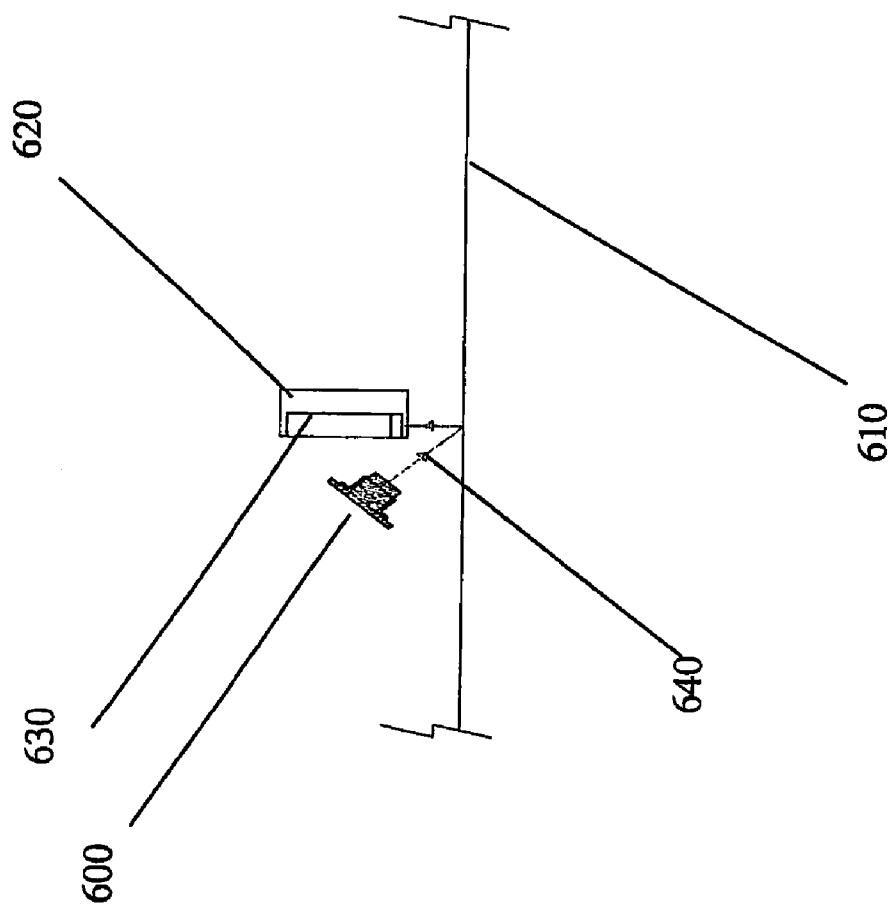
FIG. 6 shows an arrangement 60 and an optical ray diagram of an arrangement for measurement and/or defect inspection in accordance with the invention from a side view.

FIG. 6 shows a third exemplary embodiment 60 of the invention where the sheet to be inspected or measured is traversed in front of a light source 600 and a light detector array 620. In FIG. 6 the sheet 610 traverses from left to right or from right to left. In this embodiment the light source is composed of several solid-state, light emitting components such as LEDs (Light Emitting Diodes) and optical components such as light apertures, reflective surfaces, diffusing materials and other components to target the light towards the material sheet and to guarantee uniform light emission from the light source. Other light emitting devices may also be used in accordance with the invention. The LEDs typically emit light at red wavelengths but blue, white and IR (infrared) LEDs may also be used in some embodiments of the invention. The LEDs may be arranged in one or several rows and a required number of columns to cover the necessary measurement width in the inspection or measurement system. The light source also comprises electronics to receive a controlling, synchronization signal (carrier) from the waveform generator, and to control the intensity of the light emission from the LEDs or other light emitting components in such manner that the intensity follows the waveform of the waveform generator. In the exemplary embodiment 60 the waveform generated by the waveform generator is an AC sine wave voltage and a DC offset can be added to the synchronisation signal before using it for light source control. This is required to guarantee linearity of light emitters also at the AC sine wave signal values corresponding to lowest emitted light intensity.

The light detector array 620 comprises several detector modules 630, each consisting of one or more individual light detectors. For example in embodiment 40 the light detection of the inspection or measurement system is based on using a total of 18 detector modules. In the purely exemplary case of using detector modules comprising 4 light detectors, a total of 18×4=64 light detectors are used in the system.

Figure 7:
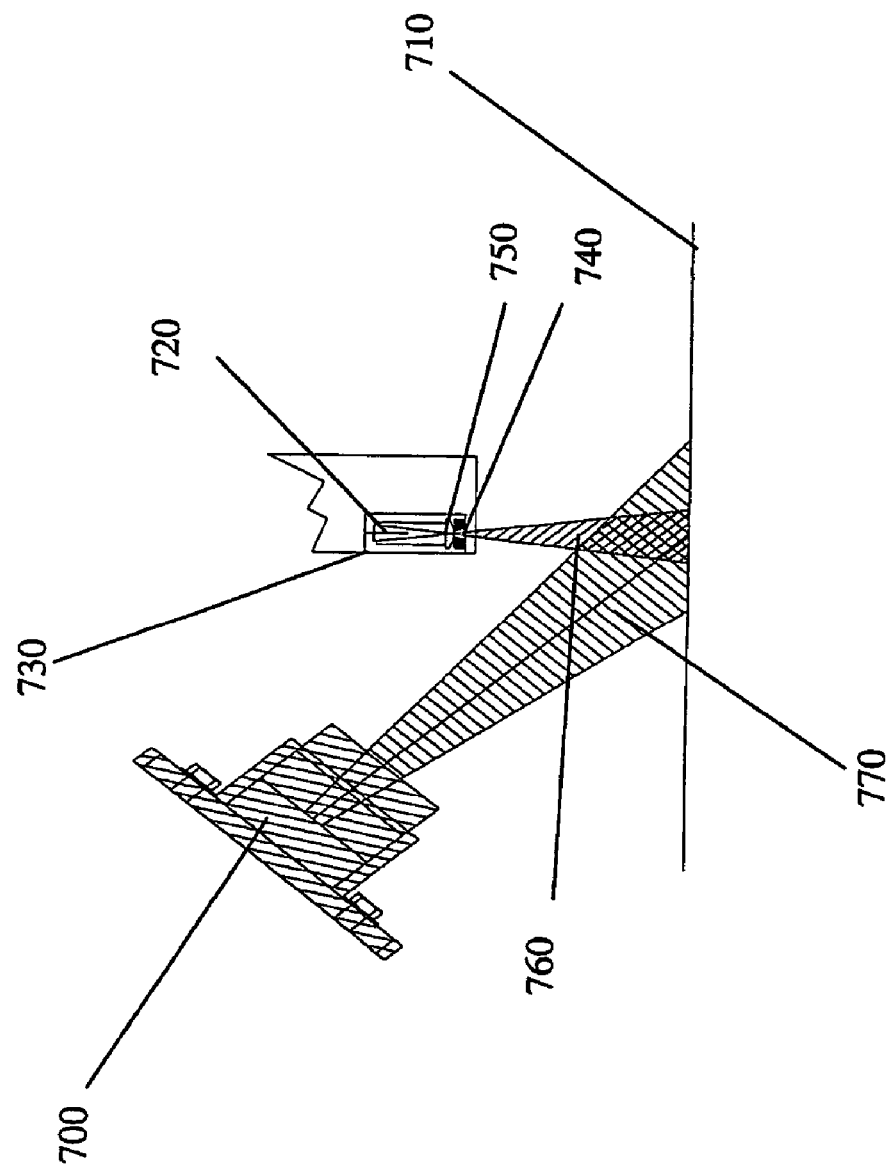
FIG. 7 shows a more detailed arrangement 70 and an optical ray diagram of an arrangement for measurements and defect inspection in accordance with the invention from a side view.

FIG. 7 displays a more detailed diagram of a light detector 720 in accordance with the invention, which is similar to arrangement 60. The viewing angle in FIG. 7 is similar to FIG. 6. In this embodiment the light detectors 720 are arranged in detector modules, each comprising four light detectors 720. FIG. 7 shows an exemplary measurement situation in which each light detector is optically arranged to have a certain, limited FOV. In this embodiment the light sensitive optical component is a silicon photodiode 730, but it may also be realised with an APD or any other photodetector in some embodiments. By using other optical components such as a light pipe 740 and a lens 750 the photodiode is arranged to have a limited FOV 760 and therefore only a certain, limited area of the material sheet is viewed by the photodiode. In this embodiment the light source 700 is arranged to emit light in a fan beam 770, which covers a material sheet area larger than the total FOV area of the light detectors. The shape of the photodiode viewing area when projected on the surface of the material sheet may be circular, elliptical, rectangular or it may have any other shape as defined by the geometrical and dimensional characteristics of the photodiode and the other optical components. When projected on the surface of the material sheet, the viewing areas of neighbouring light detectors typically overlap. The other optical components define the focusing properties of the optical path from the surface of the sheet to the active surface of the photodiode component. In some embodiments the optics of the light detector may include other optical components and any number of lenses. Optical filters may be used to limit the system operation to a distinct range of wavelengths. Several light detecting photodiodes may use a common lens to comprise several light detectors, or one integrated detector.

In the exemplary application of detecting and measuring spots in the material sheet, a light detector 720 with FOV covered by the material sheet normally views a certain limited surface area of the material sheet in a 90-degree angle in respect to the material sheet. Depending on the reflectance characteristics of the material a certain, but rather uniform amount of light, originating from the light source is reflected from the material to the light detector. The uniformity of this light signal depends on the uniformity of light reflectance from a normal, defect-free sheet of this material. A spot present in the material will inevitably pass through the FOV of one of the light detectors in the inspection or measurement system. This is guaranteed by the fact that the optical measurement system is wider than the material sheet and the FOVs of neighbouring light detectors somewhat overlap. When a spot is in the FOV of a light detector 720, light originating from the light source 700 will reflect from the spot area in a manner that differs from normal material. The light reflected from the material sheet into the FOV of the light detector 720 will be focused on the photodiode 730. Depending on spot dimensions, FOV dimensions, material sheet traversing speed, measurement geometry, optics of the light detector 720 and several other factors, presence of the spot in the FOV will result in a rapid, momentary change of varying amplitude and length in the total light intensity received by the photodiode 730. This results in a pulse type, rapid change in the photocurrent output of the photodiode. If this light pulse is considerably larger than any pulse originating from normal variations in the light reflectance properties of the material, a reliable spot detection signal may be deduced from the photocurrent output of the photodiode.

Any other defects or imperfections that have the property of reflecting light from the material in a manner clearly deviating from a normal material sheet may be detected in a similar manner. Defects or imperfections that reflect less light than the normal material, like holes, may be detected in a similar manner as dark spots. Defects or imperfections that reflect more light than the normal material may be detected in a similar manner, except that typically the polarity of the signal is different.

In another embodiment of the invention three dimensional defects or imperfections may be detected from the material sheet by using light detectors operating at different view angles in respect to the surface of the material sheet. Detection of such defects or imperfections is based on deducing the variations in the reflectance signals received by the light detectors and which originate from same surface locations of the material sheet. In an exemplary embodiment two sets of light detectors view the surface of the material sheet in 45 and 135-degree angles in respect to the speed vector of the traversing material in the plane defined by the speed vector and a vector perpendicular to the material sheet. In some exemplary embodiments the beams measure height, width and depth of the defect, in other embodiments the area, circumference or any other geometric properties of the defect.

In one preferable embodiment of the invention several emitters are synchronised to the same receiver and detector with different frequencies. The emitters and the detectors are focused to the same area. In this embodiment three dimension defects such as bumps and pits are distinguished from two-dimensional defect such as stains for example. The two-dimensional defects such as stains cause a uniform signal change for light emitted both from left and the right. However, when a three-dimensional defect, such as a bump is illuminated from the right, the defect causes a shadow to the left. Vice versa, a light from the left to a bump causes a shadow on the right. The shadows can be detected as depressions of the signal in accordance with the invention.

It is clear that the embodiments presented in FIGS. 4, 5, 6 and 7 may be combined in one actual optical measurement system. All the presented embodiments may be combined in such exemplary manner that the transmittance measurement presented in exemplary embodiment 40 may utilize common light detectors with the reflectance measurement presented in exemplary embodiment 60, and material sheet width may be measured utilizing light detectors performing transmittance and/or reflectance measurement and inspection of defects or imperfections in the material sheet. In such embodiment two light sources would emit light from opposing sides of the material sheet towards the material and light originating from both light sources would be received by the same set of light receivers and light detectors after interactions with the material sheet. It is also clear that light emitter arrays can be summed to produce signals and light detector arrays may be used to produce signals that are analysed in accordance with the invention.

Generally, in the typical embodiments of the invention the waveform (carrier) generated by the waveform generator is an AC sine wave voltage signal at a fixed frequency. However, it is clear that the waveform (carrier) signal may take a square wave form, saw tooth form, or the form of any periodic function. This control signal is utilized to synchronize the operation of one or more light sources and one or more light detectors. In the exemplary embodiments presented in FIGS. 4, 5, 6, and 7 the photoelectric currents produced by the photodiodes are fed into signal processing electronics that perform manipulation and processing on the basic photocurrent signals. The control signal (carrier) received by the signal processing electronics from the waveform generator is utilised to perform synchronised detection of the signals received from the photodiodes after signal manipulation. In some of the presented embodiments of the invention, a transimpedance amplifier is first used to convert the photocurrents of the photodiodes into photovoltages. DC components of the photovoltage signals are removed in AC coupled amplifiers. The waveform generator generates a fixed frequency AC sine wave voltage and a symmetrical, 50% duty cycle, square wave signal, processed from this sine wave signal and carrying equal frequency and phase in terms of zero-crossings, is used for rectifying the photovoltage signal after removal of the DC components. Rectified voltage signal is low-pass filtered to finalise synchronized detection or demodulation. The filter circuit used is typically a Bessel filter but it may also be a Gaussian, Chebyshev, Butterworth or an RC filter. The signal output of the signal processing (demodulated signal) is further fed into and processed by system level electronics which in these embodiments include dedicated electronics to track rapid momentary changes in the demodulated signal, which are not normal for the material to be inspected or measured. In these embodiments demodulated signal is further filtered by a low pass filter in one signal path and a comparator circuit is used to track fast changes of the demodulated signal by subtracting low-pass filtered demodulated signal and the original demodulated signal from each other. In these exemplary embodiments a certain signal difference threshold is used in the comparator to produce a digital defect pulse when e.g. a hole, a spot or other defect corresponding to the required signal threshold is measured by the system. In some embodiments several comparators with varying threshold levels are used.

In those embodiments where dimensions of the material sheet or locations of material sheet edge are measured, the absolute value of the demodulated signal is also observed and recorded. The absolute value of the demodulated signal is measured and recorded by using an analog-to-digital converter (ADC).

The digital pulses produced by the dedicated signal analysing electronics and/or digitised signal values produced by the ADC are analysed in the system level digital signal processing electronics and software. The analysis typically produces data visible to the user of the inspection or the measurement system through a computer monitor but the invented optical detection system may also be integrated with any other production systems or factory automation systems to trigger automatic actions in the production of materials manufactured in a continuous fashion.

Figure 8:
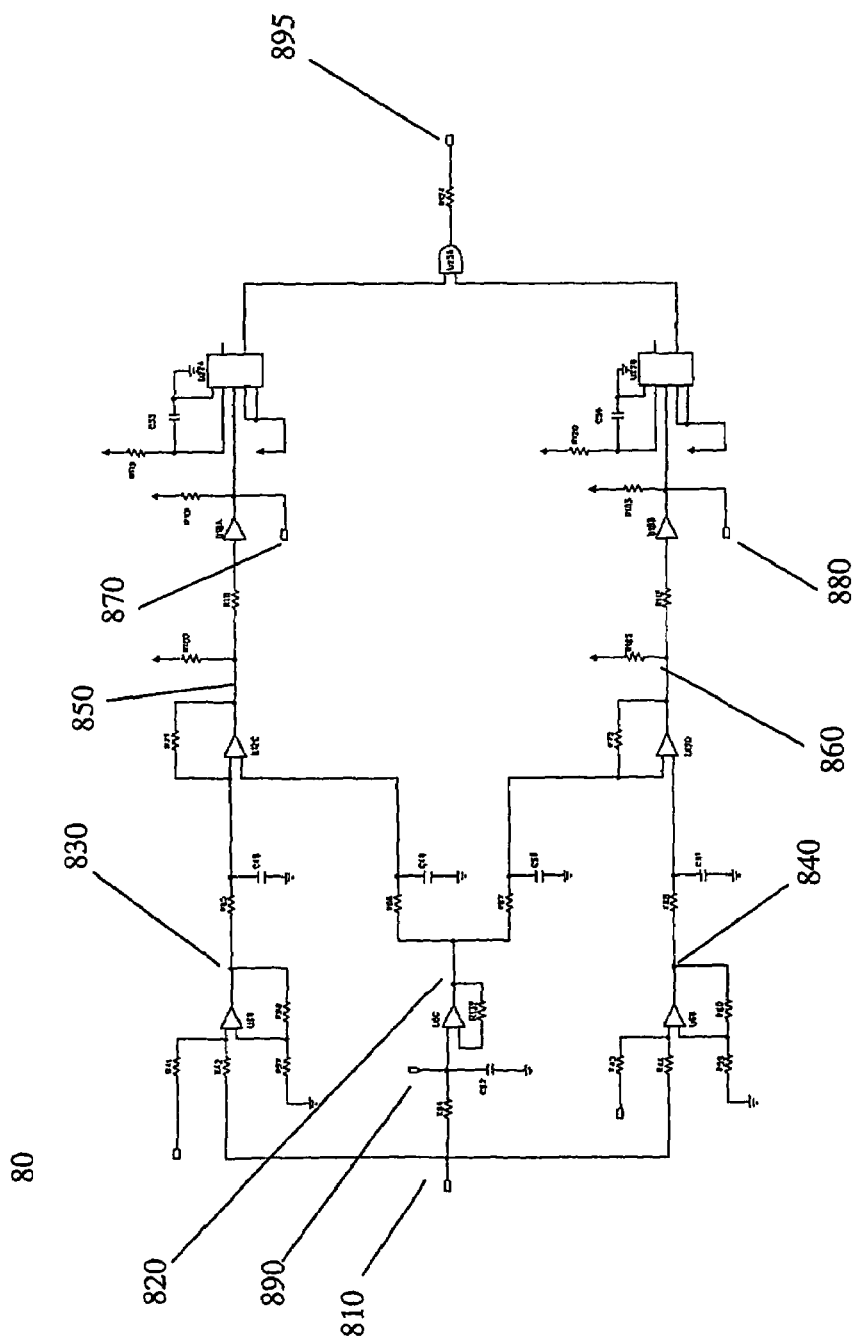
FIG. 8 shows an exemplary, functional block diagram for a fault detection circuit and method 80 in accordance with the invention.

FIG. 8 shows an exemplary, functional block diagram for a fault detection circuit and method 80 in accordance with the invention.

In 810 the demodulated voltage signal is received from the demodulation filtering. Next this signal branches to three different paths: to an amplifier 820 which adds or subtracts a selected hole detection threshold voltage, to another amplifier 823 which similarly adds or subtracts a selected spot detection threshold voltage, and to a low pass filter amplifier 825. The outputs of 820 and 823 are compared with output of 825 in comparators 830, 833, and digital hole or spot signal pulses 840, 843 will be deduced by the comparators in case analog signals exceeding the set thresholds enter the fault detection circuitry.

In many favourable embodiments the output of the low pass filter amplifier 825 needs to be reset fast in order to prevent dead time after defect pulse generation. This is required, for example, to deduce many nearly concurrent spots and/or holes in a dynamic inspection situation. In some embodiments this is achieved by feeding the digital defect signal pulses into a circuit 850, which generates a reset pulse for the low pass filter amplifier 825 immediately after receiving a digital defect signal 840 or 843. This effectively resets the fault detection circuitry right after a fault has been detected and, thus the detection of further faults may commence very dynamically indeed.

In any embodiments several beams may be used to measure several properties of the materials sheets simultaneously. This is effectively achieved in accordance with the invention when several emitters are synchronised with a detector, and the emitters emit beams with different carrier frequencies, which measure different properties from the material sheet. The different beams may also be effectively utilised in measuring the three dimensional structure of the defects.

The invention has been explained above with reference to the aforementioned embodiments, and several advantages of the invention have been demonstrated. The invention allows a more dynamical and reliable method for detecting optically visible defects, such as holes and spots in sheet materials. It has also been demonstrated that the invention may be used for the measurement of other characteristics of products manufactured in a continuous fashion, such as web or strip sheet width, length or edge position. The invention is capable of measuring several properties of the sheet and/or defect simultaneously. In addition the invention is capable of detecting the three dimensional structure of defects.

It is clear that the invention is not only restricted to those embodiments presented, but comprises all possible embodiments within the spirit and scope of the inventive thought and the following patent claims.

REFERENCES

GB 2181834
GB 2087544

The invention claimed is:

1. An optical measurement and inspection method comprising:
providing at least two light emitters,
providing at least one light receiver,
providing at least one signal generator connected to at least one of the light emitters and the at least one light receiver, and
providing means for converting the received light to electrical current, wherein
providing a sheet of material that lies or traverses between and/or in front of the at least two light emitters and the at least one light receiver (200),
controlling, with the at least one signal generator, at least one of the light emitters and the at least one light receiver by sending them an electronic synchronisation signal and thereby synchronises emission and detection of light rays (205, 215, 245), fixing a common carrier waveform AC voltage signal in frequency, and a symmetrical 50% duty cycle wave signal is processed from the common carrier AC voltage waveform signal and the common carrier waveform AC voltage signal and the 50% duty cycle wave signal carry equal frequency and phase in terms of zero-crossings, driving, with the at least one signal generator, the at least two light emitters with different carrier frequencies waveforms and/or phases, and the at least one light receiver with both of these frequencies, waveforms and/or phases, emitting, with the at least two light emitters, at least two rays of light (220), the at least two rays of light being incident on the stationary or traversing sheet (225), detecting by the same light receiver (230) at least two rays of light grazing the sheet, transparent to the sheet, reflected from the sheet or directly from the light emitters, an intensity of at least one said emitted ray of light follows at least one of the carrier waveform signals and at least one said detected light ray is demodulated from the carrier waveform signal using the electronic synchronisation signal, converting at least two of the rays of light to photocurrent (240), and rectifying photocurrent signal with the symmetrical wave signal, processed from the common carrier waveform signal, removing at least one DC component from the photocurrent signal, and diagnosing and observing the processed photocurrent and/or changes in the processed photocurrent to find defects and/or determine characteristics of the said sheet of material (250), wherein at least one said carrier waveform signal is a sine wave, cosine wave, or a square wave signal.

2. The optical measurement and inspection method in accordance with claim 1, wherein different rays of light from different emitters targeted to the same receiver measure different properties of the material sheet.

3. The optical measurement and inspection method in accordance with claim 2, wherein a three dimensional structure of a defect is detected with more than one of the rays of light.

4. The optical measurement and inspection method in accordance with claim 1, further comprising converting the photocurrent to a voltage upon rectifying the photocurrent signal.

5. The optical measurement and inspection method in accordance with claim 4, further comprising amplifying the resulting photocurrent or voltage upon detecting by the same light receiver.

6. The optical measurement and inspection method in accordance with claim 1, further comprising feeding the resulting photocurrent or a voltage converted from the photocurrent during rectifying into a fault detection circuit (80) that comprises:

means for summing 820, 823 a positive or negative threshold voltage value to the voltage signal entering the fault detection circuit, a low pass filter signal path (825), means for resetting the circuit (850), means for generating digital defect signal pulses 840, 843 when signals exceeding preset threshold values are produced by demodulation- or synchronised detection circuitry of the measurement and inspection method.

7. The optical measurement and inspection method in accordance with claim 1, wherein the sheet material (410, 510, 610, 710) is paper, steel, plastic, metal, rubber, aluminium foil, copper foil, film, or coated metal sheet.

8. The optical measurement and inspection method in accordance with claim 1, wherein location and/or size of at least one defect and/or other attributes of at least one defect and/or sheet width, thickness, length, density, reflectivity, purity or other physical attributes of the sheet are derived from optical measurements performed by the method.

9. The optical measurement and inspection method in accordance with claim 1, wherein the arrangement is configured to detect one or more defects that feature aspects of the following: holes, pinholes, scratches, spots, stains, cracks, edge faults, streaks, or surface faults.

10. The optical measurement and inspection method in accordance with claim 1, wherein at least one light detector (520, 570, 720), a detector module (430, 560, 630) or a detector array (420, 620) comprise at least one photoelectric device (530, 730), lens (550, 750) or wave guide (540, 740).

11. The optical measurement and inspection method in accordance with claim 1, wherein the signal generator drives at least two light receivers with different carrier frequencies, waveforms and/or phases.

12. An optical measurement and inspection arrangement, comprising:

at least two light emitters, at least one light receiver, at least one signal generator connected to at least one of the light emitters and at least one of the light receivers, and means for converting the received light to electrical current, wherein a sheet of material (410, 510, 610, 710) is arranged between and/or in front of the at least two light emitters (400, 500, 600, 700) and the at least one light receiver (420, 520, 620, 720), the at least two light emitters (400, 500, 600, 700) are arranged to emit at least two rays of light incident on at least one sheet, at least two rays of light grazing the sheet, transparent to the sheet or reflected from the sheet are arranged to be detected by the same at least one light receiver (420, 520, 620, 720), at least one ray of light is arranged to be converted to photocurrent by at least one photoelectric device (530, 630, 730)

the at least one signal generator is arranged to control at least one of the light emitters (400, 500, 600, 700) and at least one of the light receivers (420, 520, 620, 720) by sending them an electronic synchronisation signal and thereby synchronises the emission and detection of rays, a common carrier waveform AC voltage signal is fixed in frequency, and a symmetrical 50% duty cycle wave signal is processed from the common carrier AC voltage waveform signal and the common carrier waveform AC voltage signal and the 50% duty cycle wave signal carry equal frequency and phase in terms of zero/crossings, the at least one signal generator is arranged to drive the at least two light emitters with different carrier frequencies, waveforms and/or phases, and the at least one light receiver with both of these frequencies waveforms and/or phases, an intensity of at least one said emitted ray of light is arranged to follow at least one of the carrier waveform signals and at least one received light ray is arranged to be demodulated from the carrier waveform signal using the electronic synchronisation signal, the symmetrical wave signal, processed from the common carrier waveform signal, is configured for rectifying photocurrent signal, at least one DC component is removed from the photocurrent signal, and the photocurrent and/or changes in photocurrent are arranged to be diagnosed and observed to find defects and/or determine characteristics of the said sheet of material (310), wherein at least one of said carrier waveform signal is a sine wave, cosine wave, or a square wave signal.

13. The optical measurement and inspection arrangement in accordance with claim 12, wherein different rays of light from different emitters arranged to be targeted to the same receiver are arranged to measure different properties from the material sheet.

14. The optical measurement and inspection arrangement in accordance with claim 12, wherein a three dimensional structure of a defect is arranged to be detected with more than one of the rays of light.

15. The optical measurement and inspection arrangement in accordance with claim 12, further comprising feeding the resulting photocurrent or a voltage converted from the photocurrent during rectifying into a fault detection circuit (80) that comprises, means for summing a positive or negative threshold voltage value to the voltage signal entering the fault detection circuit 820, 823, a low pass filter signal path (825), means for resetting the circuit (850), and means for generating digital defect signal pulses 840, 843 when defect signals exceeding preset threshold values are produced by demodulation- or synchronised detection circuitry of the measurement and inspection arrangement.

16. The optical measurement and inspection arrangement in accordance with claim 12, wherein the sheet material (310, 410, 510, 610) is paper, steel, plastic, metal, rubber, aluminium foil, copper foil, film or coated metal sheet.

17. The optical measurement and inspection arrangement in accordance with claim 12, wherein a location and/or size of at least one defect or other attributes of at least one defect or sheet width, thickness, length, density, reflectivity, purity or other physical attributes of the sheet are derived from optical measurements performed by the arrangement.

18. The optical measurement and inspection arrangement in accordance with claim 12, wherein the arrangement is configured to detect one or more defects that feature aspects of the following: holes, pinholes, scratches, spots, stains, cracks, edge faults, streaks, or surface faults.

19. The optical measurement and inspection arrangement in accordance with claim 12, wherein at least one of said light receivers or means for converting the received light (420, 520, 560, 570, 620, 630, 720) comprises at least one photodetector (530, 730), lens (550, 750) or wave guide (540, 740).

20. The optical measurement and inspection arrangement in accordance with claim 12, wherein the signal generator is arranged to drive at least two light receivers with different carrier frequencies, waveforms and/or phases.

* * * * *

UNITED STATES PATENT AND TRADEMARK OFFICE
CERTIFICATE OF CORRECTION

PATENT NO. : 7,605,921 B2  Page 1 of 1
APPLICATION NO. : 10/533645
DATED : October 20, 2009
INVENTOR(S) : Hietanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 397 days.

Signed and Sealed this

Fifth Day of October, 2010

David J. Kappos
*Director of the United States Patent and Trademark Office*